United States Patent [19]
Lindstam

[11] Patent Number: 4,808,179
[45] Date of Patent: Feb. 28, 1989

[54] CONTAINER DEVICE AND A METHOD FOR MANUFACTURING OF THE DEVICE

[75] Inventor: Göran Lindstam, Lund, Sweden

[73] Assignee: AB Akerlund & Rausing, Sweden

[21] Appl. No.: 22,506

[22] Filed: Mar. 9, 1987

Related U.S. Application Data

[63] Continuation of Ser. No. 729,251, May 1, 1985, abandoned.

[30] Foreign Application Priority Data

May 9, 1984 [SE] Sweden ............................... 8402509

[51] Int. Cl.[4] ............................................ A61B 19/00
[52] U.S. Cl. ..................................... 604/408; 53/450; 426/412
[58] Field of Search ................. 604/411, 414, 415, 88, 604/244, 262, 408, 412, 413; 426/410, 412, 413, 414; 53/425, 450, 459, 475, 202, 567

[56] References Cited

U.S. PATENT DOCUMENTS

| | | | |
|---|---|---|---|
| 2,689,564 | 9/1954 | Adams et al. | 604/412 |
| 2,704,075 | 3/1955 | Cherkin | 604/408 |
| 2,884,988 | 5/1959 | D'Angelo | 53/479 |
| 2,940,230 | 6/1960 | Flax | 53/479 |
| 2,949,712 | 8/1960 | Bieberdorf et al. | 604/408 |
| 3,030,955 | 4/1962 | Gossett et al. | 604/408 |
| 3,306,563 | 2/1967 | Soto | 604/88 |
| 3,343,541 | 9/1967 | Bellamy, Jr. | 604/408 |
| 3,403,064 | 9/1968 | Bellamy | 53/479 |
| 3,509,879 | 5/1970 | Bathish et al. | 604/408 |
| 3,648,693 | 3/1972 | Koremura | 604/411 |
| 3,685,795 | 8/1972 | Caster | 604/244 |
| 3,776,798 | 12/1973 | Milano | 53/450 |
| 4,183,964 | 1/1980 | Vinokur | 426/413 |
| 4,216,639 | 8/1980 | Gautier | 426/410 |
| 4,223,043 | 9/1980 | Johnson | 426/413 |
| 4,257,535 | 3/1981 | Mellett | 53/479 |
| 4,363,205 | 12/1982 | Hollander, Jr. | 426/413 |
| 4,384,440 | 5/1983 | Ohlsson | 426/410 |
| 4,543,769 | 10/1985 | Schmitz | 53/450 |
| 4,709,534 | 12/1987 | Sengewald | 53/450 |

FOREIGN PATENT DOCUMENTS

| | | | |
|---|---|---|---|
| 1070250 | 7/1954 | France | 604/415 |
| 0892210 | 3/1962 | United Kingdom | 604/415 |

*Primary Examiner*—C. Fred Rosenbaum
*Assistant Examiner*—Kathleen Daley
*Attorney, Agent, or Firm*—Lerner, David, Littenberg, Krumholz & Mentlik

[57] ABSTRACT

The present invention discloses a flexible container device which forms a sterile system comprising a pouch-shaped container and a hose shaped connector. The container is characterized in that it comprises a tear-away first cover layer, for instance a tape, arranged over at least one sterile point of connection of at least one of said hose shaped connectors. The connecting end of the hose has a second cover layer placed over a sterile device for mounting the hose onto the container. An external grip device is arranged from the other end of the hose and is operatively connected to a puncturing device inside the hose which puncturing device punctures the container after the hose has been mounted thereon, thereby maintaining the system in a generally sterile condition. Also disclosed is a method for manufacturing said device.

3 Claims, 1 Drawing Sheet

CONTAINER DEVICE AND A METHOD FOR MANUFACTURING OF THE DEVICE

This is a continuation of application Ser. No. 729,251 filed May 1, 1985 now abandoned.

FIELD OF THE INVENTION

The present invention relates to a flexible container and a method for manufacture thereof. More precisely, the invention relates to a device comprising a pouch-shaped container and a hose type connector. The container device is designed principally for use in medical fields.

BACKGROUND OF THE INVENTION

Flexible container devices comprising a softened P.V.C. pouch provided with a connector hose are extant in the prior art. The pouches of these devices are filled with a liquid, e.g. an infusion liquid, and are packed in an outer patch which is put under light vacuum. Thereafter, the devices are batch autoclaved.

The design of the instant flexible container seeks to eliminate in a reliable way as many of the sources of error in use of the prior art flexible container devices as can reasonably be eliminated and, moreover, the instant invention seeks to permit the patient to assemble as much of the flexible container device as possible without assistance. The object of the invention, therefore, is to eliminate the more complicated design aspects of prior flexible container devices and provide a system that is straight-forward and which can be optimally operated in a non-cumbersome way.

SUMMARY OF THE INVENTION

In a sterile system, liquid is filled into a series of pouch-shaped containers part of which comprise a web. The web-like structure is capable of being sterilized in line. The hose shaped web is welded and individual flexible pouch-shaped containers are punched out from the web.

The present invention disclose an apparatus for forming a sterile connection with a flexible container formed from a flexible hose-shaped web. The container includes at least one sterile connection location adapted for connection with a connecting hose. The apparatus comprises a first tear-away cover strip removably covering at least one sterile connection location on the flexible container. The hose member comprises a first end and a second end. The first end of the hose member includes a cover plate means sealably closing the first end of the hose member. The cover plate means includes an outer surface, and an adhesive means on the outer surface of the cover plate means. A second tear-away cover strip removably covers the outer surface of the cover plate means. Upon the removal of the second tear-away cover strip from the outer surface of the cover plate means said first end of said hose member may be adhesively mounted at at least one sterile connection location on the flexible container. The second end of the hose member, which includes the gripping means permitting the second end of the hose member to be firmly gripped from its outer surface. The apparatus also comprises puncturing means mounted within the hose member. The puncturing means faced the first end of the hose member and are operatively connected to the gripping means at the second end of the hose member. Upon removal of the first and second tear-away cover strips and upon the mounting of the hose member at at least one sterile location of the flexible container, the flexible container may be punctured by the puncturing device while still maintaining the flexible container and the hose member in a generally sterile condition.

The puncturing device is comprised of a blade having a cutting edge supported by a support device. The support device is a specified distance from the grip device so that the support device may be easily operated using the grip device. Further, the hose may be made of bendable materials.

Also disclosed herein is a method for manufacturing a plurality of flexible containers adapted for sterile connection with a connecting hose. The method comprises providing a flexible web including a plurality of sterile connection locations adapted for connection with said connecting hose on a predetermined path along the flexible web. A tear-away cover strip means is applied along the pre-determined path. The tear-away cover strip means removably covers the plurality of sterile connection locations. The flexible web is then formed into the shape of a hose. A plurality of individual flexible containers is thus formed within the hose shaped flexible web. Each plurality of individual flexible containers is separated from adjacent ones by weld seams. In the course of said separation, each individual flexible container includes at least one of said plurality of sterile connection locations. Each individual flexible container is filled with sterile liquid. The entire hose shaped flexible web, including a plurality of individual flexible containers containing said sterile liquid and including said tear-away cover strip means are sterilized. Following sterilization, the plurality of individual flexible containers is separated along said weld seams. Said sterilization may be carried out in line with the filling of the flexible containers. Moreover, the weld seams may further comprise holes for supporting said flexible containers.

DESCRIPTION OF PREFERRED EMBODIMENT

The hose, 10, is made of a flexible material having good steam and gas barrier properties, and being resistant to sterilizing heat temperatures in the range of 120° C. to 150° C. Several suitable laminates are known in this regard which are based on polypropylene, preferably HD polypropylene, polyvinylidienchloride, polyamide, and metal foil, possibly in combination with a suitable sealing layer. The holds for accessing the liquid carried by the hose are protected by a tear-away layer, in the present case a tear-away tape strip, 11, attached longitudinally upon the hose. The tape 11 is attached to the hose such that locations 12 for connecting a hose shaped connector (shown in FIG. 2) are covered. However, there is no requirement that the tape should be an integral strip in the longitudinal direction of the hose. The basic requirement is that each location of a connecting hose, whether it be at one or several locations for each individual container, is covered by a protective cover layer.

The transport direction of the hose is indicated by the arrow, 13. A known apparatus is provided for forming the web, filling the hose, and sterilizing both internally and externally the hose and the contents thereof. Similarly, a known apparatus is used for forming the individual flexible pouch-shaped containers and for separating said containers. The cover strip, 11, whether integral or comprising individual pieces, is attached to the hose at the input side of the filling and sterilizing device. The locations for connection of the hose, 12, may be premarked, possibly by weakening lines, so that there will be no doubt as to where to mount the hose containing a puncturing device shown in FIG. 2.

Figure 1:
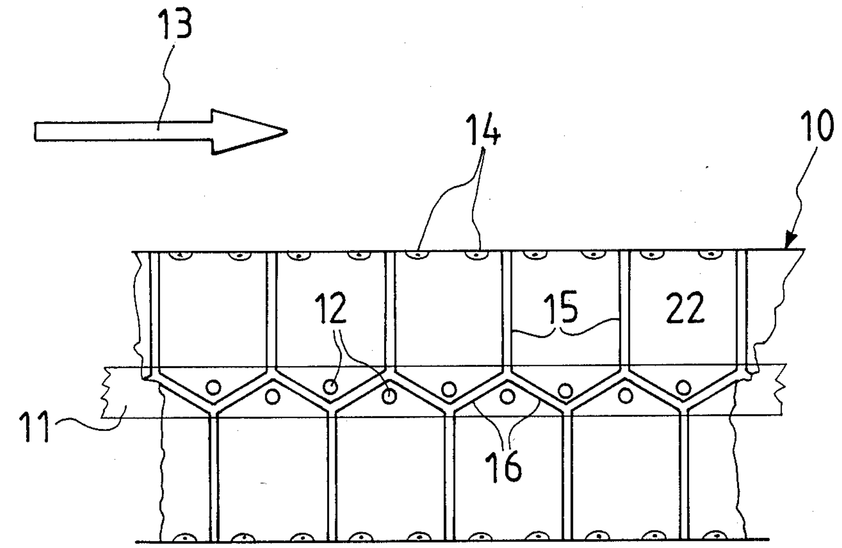
FIG. 1 schematically represents a set of individual containers forming a hose shaped web.

FIG. 1 also shows how the hose shaped connector ends, that is the ends of the connecting hose, are formed and welded in a zigzag pattern to minimize material waste. The hose further comprises holes, 14, for supporting the container in the bottom region of each individual container. Preferably said holes are formed when the weld seams 15 and 16 are realized. In the present case such weld seams indicate two adjacent rows of containers, but it is understood that the weld seams, and the individual flexible containers, may be obtained in several different ways.

Figure 2:
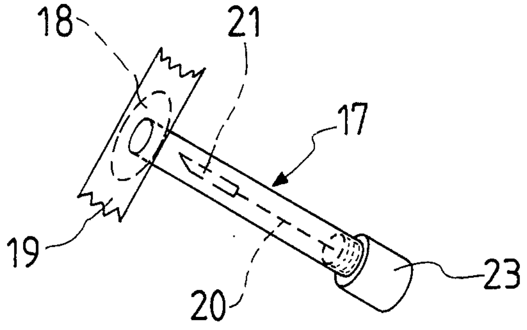
FIG. 2 schematically shows a hose shaped connector device provided with a means for puncturing individual containers.

The hose connector, 17, shown in FIG. 2 consists of a soft resilient material, for instance softened P.V.C., and has a plate, 18, attached at the mounting end. The mounting side of the plate has an adhesive coating applied to it, said coating comprising any adhesive means. The adhesive coating is covered by a tear-away strip, 19.

At the other end of the hose from the mounting end is a grip device, 23, that is removably attached to the hose. Any means for attaching the gripping device is satisfactory. The currently preferred embodiment, the gripping device, is attached by threads. The grip device is provided with a support, 20, for supporting the puncturing means, 21. The puncturing device may be any tool having the capability of puncturing for instance a tool having a knife-like edge for a punch. The support, 20, is dimensioned such that it places the edge, 21, at a designated distance from the plate, 18.

The arrangement comprising the hose, the attachment plate, and the knife is delivered as a sterile unit in a sterile container. Containers, 22, are delivered filled with liquid, for instance an infusion liquid, and are provided with a cover layer strip over the location or locations of the hose shaped connectors. The mounting of the plate, 18, at location 12 is carried out immediately after removing the cover strip, 11, and the strip, 19. This provides for a nearly unbroken sterile environment for the pouch, 22, and the hose, 17. Puncturing then occurs by means of the puncturing device, 21. The grip portion, 23, and the knife are removed, and the hose is immediately connected to the input terminal of the body. In the case of using this container device for purposes of dialysis, the hose is connected to the belly cavity.

I claim:

1. A method of manufacturing filled containers comprising the steps of:

(a) providing a flexible tube filled with liquid, the wall of said tube having longitudinally spaced-apart connection regions each adapted for connection to a discharge device, said tube having releasably adhering thereto a cover layer in the form of at least one continuous tape extending longitudinally along said flexible tube, and overlaying a plurality of said regions;

(b) advancing the liquid-filled flexible tube with said cover layer through a sterilizer and sterilizing said tube, said liquid and said cover layer in said sterilizer;

(c) forming lateral weld seams extending across said tube to thereby subdivide said filled tube and said cover layer into a plurality of individual containers each including one of said connection regions and having thereon a portion of said cover layer; and (d) separating said containers from one another and said portions of said cover layer from one another along said weld seams, the method further comprising the step of forming a weld seam extending longitudinally along said tube before said separating step so that said longitudinal seam cooperaties with said lateral weld seams in subdividing said filled tube and said tape into a plurality of individual containers, said separating said including the step of separating said containers and portions of said cover layer from one another along both said lateral weld seams and said longitudinal weld seam, said step of forming said longitudinal weld seam being performed so that said longitudinal weld seam is formed in a region of said tube covered by said tape, whereby said tape is subdivided along said longitudinal weld seam.

2. A method as claimed in claim 1 wherein said step of forming said longitudinal weld seam include the step of forming said longitudinal weld seam in a zigzag pattern including alternating corners pointing in opposite directions, said step of forming said lateral weld seams including the step of forming said lateral weld seams so that each lateral weld seam extends from one corner of said zigzag longitudinal seam.

3. A method of manufacturing filled containers commprising the steps of:

(a) providing a flexible tube filled with liquid, the wall of said tube having longitudinally spaced-apart connection regions each adapted for connection to a discharge device, said tube having releasably adhering thereto a cover layer in the form of at least one continuous tape extending longitudinally along said flexible tube, and overlaying a plurality of said regions;

(b) advancing the liquid-filled flexible tube with said cover layer through a sterilizer and sterilizing said tube, said liquid and said cover layer in said sterilizer;

(c) forming lateral weld seams extending across said tube to thereby subdivide said filled tube and said cover layer into a plurality of individual containers each including one of said connection regions and having thereon a portion of said cover layer; and (d) separating said containers from one another and said portions of said cover layer from one another along said weld seams, said step of providing a flexible tube filled with liquid including the steps of providing a flexible web having said connection locations arranged along a predetermined path on said flexible web, applying said tape to said web along said predetermined path and then forming said web into said flexible tube.

* * * * *